(12) United States Patent
Irvin et al.

(10) Patent No.: US 9,138,502 B2
(45) Date of Patent: Sep. 22, 2015

(54) AIR FRESHENER WITH DECORATIVE INSERT

(71) Applicant: American Covers, Inc., Draper, UT (US)

(72) Inventors: Aaron Irvin, Salt Lake City, UT (US); Nate Finlay, Lehi, UT (US)

(73) Assignee: American Covers, Inc., Draper, UT (US)

( * ) Notice: Subject to any disclaimer, the term of this patent is extended or adjusted under 35 U.S.C. 154(b) by 105 days.

(21) Appl. No.: 14/039,656

(22) Filed: Sep. 27, 2013

(65) Prior Publication Data

US 2014/0110497 A1 Apr. 24, 2014

Related U.S. Application Data

(60) Provisional application No. 61/717,527, filed on Oct. 23, 2012, provisional application No. 61/717,520, filed on Oct. 23, 2012.

(51) Int. Cl.
*A61L 9/12* (2006.01)
*A61L 9/04* (2006.01)
*A61L 2/00* (2006.01)
*A61L 9/00* (2006.01)

(52) U.S. Cl.
CPC ... *A61L 9/12* (2013.01); *A61L 2/00* (2013.01); *A61L 9/00* (2013.01)

(58) Field of Classification Search
CPC .............. A61L 2/00; A61L 9/00; A61L 9/04; A61L 9/12
See application file for complete search history.

(56) References Cited

U.S. PATENT DOCUMENTS

| D176,671 | S |   | 4/1876 | Myers |
|---|---|---|---|---|
| 369,878 | A |   | 9/1887 | Palmer |
| 1,171,737 | A |   | 2/1916 | Madgan |
| 1,683,545 | A |   | 9/1928 | Harris |
| D140,109 | S |   | 1/1945 | Pierce |
| 2,557,432 | A | * | 6/1951 | Holstedt ................ 96/148 |
| 2,733,333 | A |   | 1/1956 | Peters |
| D177,826 | S |   | 5/1956 | Katz |
| D178,237 | S |   | 7/1956 | Katz |
| 3,138,432 | A | * | 6/1964 | Kleinhans ................ 422/122 |

(Continued)

FOREIGN PATENT DOCUMENTS

| CA | 2077251 | 5/1993 |
|---|---|---|
| EP | 0 348 970 | 1/1990 |

(Continued)

OTHER PUBLICATIONS

U.S. Appl. No. 29/452,344, filed Apr. 15, 2013; Aaron Irvin; notice of allowance mailed Apr. 28, 2014.

(Continued)

*Primary Examiner* — Darren W Gorman
(74) *Attorney, Agent, or Firm* — Thorpe North & Western LLP (57) ABSTRACT

An air freshener device includes a rigid body or insert having a front face with a protrusion, a rear opposite the front face with a cavity corresponding to the protrusion, and an annular perimeter lip circumscribing the front face. A scent material is interspersed within the body. A flexible cover or shell extends across the rear of the body and covers the cavity, and has an inward facing annular groove surrounding and receiving the annular perimeter lip.

17 Claims, 5 Drawing Sheets

(56) References Cited

U.S. PATENT DOCUMENTS

| | | | |
|---|---|---|---|
| 3,239,145 | A | 3/1966 | Aurelio |
| 3,456,106 | A | 7/1969 | Gluschkin |
| 3,552,632 | A | 1/1971 | Wilson |
| 3,655,129 | A | 4/1972 | Seiner |
| 3,847,305 | A | 11/1974 | Tobin |
| 3,948,445 | A | 4/1976 | Andeweg |
| 3,971,858 | A | 7/1976 | Collier et al. |
| D246,986 | S | 1/1978 | Costello |
| 4,084,079 | A | 4/1978 | Costello |
| D250,041 | S | 10/1978 | Schimanski |
| 4,149,675 | A | 4/1979 | Van Breen et al. |
| 4,184,099 | A | 1/1980 | Lindauer et al. |
| 4,226,944 | A | 10/1980 | Stone et al. |
| D258,511 | S | 3/1981 | Ashton |
| 4,280,649 | A | 7/1981 | Montealegre |
| 4,301,949 | A | 11/1981 | Palson et al. |
| 4,382,548 | A | 5/1983 | van de Heijden |
| 4,391,781 | A | 7/1983 | van Lit |
| 4,517,326 | A | 5/1985 | Cordts et al. |
| 4,549,693 | A | 10/1985 | Barlics |
| 4,594,380 | A | 6/1986 | Chapin et al. |
| D286,323 | S | 10/1986 | Haworth |
| 4,638,057 | A | 1/1987 | Takahashi et al. |
| 4,649,046 | A | 3/1987 | Kross |
| 4,703,070 | A | 10/1987 | Locko et al. |
| RE32,834 | E | 1/1989 | Cordts et al. |
| 4,808,347 | A | 2/1989 | Dawn |
| 4,840,773 | A | 6/1989 | Wade |
| 4,849,606 | A | 7/1989 | Martens et al. |
| 4,869,407 | A * | 9/1989 | Booth et al. ................. 222/3 |
| 4,874,129 | A | 10/1989 | DiSapio et al. |
| 4,880,690 | A | 11/1989 | Szycher et al. |
| 4,950,542 | A | 8/1990 | Barker |
| 4,968,456 | A | 11/1990 | Muderlak et al. |
| 5,008,115 | A | 4/1991 | Lee et al. |
| 5,019,434 | A | 5/1991 | Matsumoto |
| 5,034,222 | A | 7/1991 | Kellett et al. |
| D319,781 | S | 9/1991 | Halm et al. |
| 5,050,798 | A | 9/1991 | Sullivan |
| D322,558 | S | 12/1991 | Halm et al. |
| 5,071,704 | A | 12/1991 | Fischel-Ghodsian |
| 5,114,625 | A | 5/1992 | Gibson |
| 5,120,583 | A | 6/1992 | Garcia |
| 5,178,327 | A | 1/1993 | Palamand et al. |
| 5,180,107 | A | 1/1993 | Lindauer |
| 5,193,445 | A | 3/1993 | Ferguson |
| D334,975 | S | 4/1993 | Bunce |
| 5,220,636 | A | 6/1993 | Chang |
| D338,519 | S | 8/1993 | Peterson |
| 5,234,162 | A | 8/1993 | Sullivan |
| 5,240,487 | A | 8/1993 | Kung |
| D349,157 | S | 7/1994 | Rymer |
| D350,082 | S | 8/1994 | Tietz et al. |
| D350,192 | S | 8/1994 | Patel et al. |
| 5,368,822 | A | 11/1994 | McNeil |
| 5,407,642 | A | 4/1995 | Lord |
| 5,422,078 | A | 6/1995 | Colon |
| D366,107 | S | 1/1996 | Shaffer |
| D367,526 | S | 2/1996 | Bignon |
| D367,924 | S | 3/1996 | Patel et al. |
| 5,520,921 | A | 5/1996 | Chalifoux |
| D373,626 | S | 9/1996 | Dente et al. |
| D375,350 | S | 11/1996 | Patel et al. |
| 5,595,194 | A | 1/1997 | Talbot |
| D380,258 | S | 6/1997 | Muller et al. |
| 5,651,522 | A | 7/1997 | Davis et al. |
| D382,050 | S | 8/1997 | Hayes |
| 5,683,285 | A | 11/1997 | Wong |
| 5,695,692 | A | 12/1997 | Kennedy |
| 5,704,832 | A | 1/1998 | Borrell |
| D390,941 | S | 2/1998 | Cessaroni et al. |
| D392,032 | S | 3/1998 | Zaragoza et al. |
| 5,725,152 | A | 3/1998 | Akyu |
| 5,735,460 | A | 4/1998 | Eisenbraun |
| 5,762,549 | A | 6/1998 | Scheuer et al. |
| 5,780,527 | A | 7/1998 | O' Leary |
| 5,794,767 | A | 8/1998 | Wilson |
| 5,820,791 | A | 10/1998 | Canale |
| D400,662 | S | 11/1998 | Davis |
| 5,845,847 | A | 12/1998 | Martin et al. |
| 5,860,552 | A | 1/1999 | Culhane et al. |
| 5,861,128 | A | 1/1999 | Vick et al. |
| D404,957 | S | 2/1999 | Cheris et al. |
| 5,871,765 | A | 2/1999 | Johnson et al. |
| 5,899,382 | A | 5/1999 | Hayes |
| D410,540 | S | 6/1999 | Pinchuk |
| D411,002 | S | 6/1999 | Farmer |
| D415,267 | S | 10/1999 | Kauzlarich et al. |
| D415,268 | S | 10/1999 | Farmer |
| 5,988,520 | A | 11/1999 | Bitner |
| D417,727 | S | 12/1999 | Christianson |
| 6,044,202 | A | 3/2000 | Junkel |
| D424,677 | S | 5/2000 | Chen |
| D425,190 | S | 5/2000 | Morikawa |
| 6,102,660 | A | 8/2000 | Lee |
| 6,111,055 | A | 8/2000 | Berger et al. |
| 6,123,906 | A | 9/2000 | Farmer |
| 6,123,935 | A | 9/2000 | Wefler et al. |
| D432,222 | S | 10/2000 | Rymer et al. |
| D435,694 | S | 12/2000 | Lebherz |
| D437,038 | S | 1/2001 | Chuan |
| D437,041 | S | 1/2001 | Eisenbraun |
| D437,924 | S | 2/2001 | Wu |
| 6,190,607 | B1 | 2/2001 | Farmer |
| 6,191,197 | B1 | 2/2001 | Wang et al. |
| 6,197,263 | B1 | 3/2001 | Blount |
| 6,202,938 | B1 | 3/2001 | Collier |
| D440,294 | S | 4/2001 | Bilek |
| D441,441 | S | 5/2001 | Upson |
| 6,264,887 | B1 | 7/2001 | Farmer |
| 6,291,371 | B1 | 9/2001 | Shefer et al. |
| 6,309,715 | B1 | 10/2001 | Lindauer et al. |
| 6,325,475 | B1 | 12/2001 | Hayes et al. |
| D454,190 | S | 3/2002 | Trocola |
| 6,357,260 | B1 | 3/2002 | Lutz |
| 6,374,044 | B1 | 4/2002 | Freidel |
| 6,375,966 | B1 | 4/2002 | Maleeny et al. |
| 6,379,689 | B1 | 4/2002 | Aguadisch |
| 6,391,398 | B1 | 5/2002 | Pesu et al. |
| 6,416,043 | B1 | 7/2002 | Elsenbraun |
| 6,514,467 | B1 | 2/2003 | Bulsink et al. |
| D472,968 | S | 4/2003 | Christianson |
| D476,726 | S | 7/2003 | Rosenberg |
| D478,379 | S | 8/2003 | Talenton et al. |
| D478,973 | S | 8/2003 | Wagner |
| D479,592 | S | 9/2003 | Lammel et al. |
| D479,742 | S | 9/2003 | Hollingsworth |
| D485,343 | S | 1/2004 | Wu |
| D487,504 | S | 3/2004 | Yuen |
| 6,712,286 | B2 | 3/2004 | Baxter et al. |
| D488,214 | S | 4/2004 | Quantin |
| D488,548 | S | 4/2004 | Lablaine |
| D491,257 | S | 6/2004 | Picken |
| D491,798 | S | 6/2004 | Buthier |
| D496,720 | S | 9/2004 | Dudley |
| 6,800,252 | B1 | 10/2004 | Jedzinski |
| 6,830,733 | B2 | 12/2004 | Stanley, III |
| 6,885,811 | B2 | 4/2005 | He et al. |
| D504,943 | S | 5/2005 | Dudley |
| D507,341 | S | 7/2005 | Taylor |
| D511,568 | S | 11/2005 | Wheatley |
| D514,679 | S | 2/2006 | Wheatley |
| D515,192 | S | 2/2006 | Smith et al. |
| 7,025,283 | B2 | 4/2006 | Torres |
| 7,055,764 | B1 | 6/2006 | Martinez et al. |
| 7,061,386 | B2 | 6/2006 | Seresini |
| 7,070,172 | B2 | 7/2006 | Febraga et al. |
| 7,137,570 | B2 | 11/2006 | Wheatley et al. |
| D535,376 | S | 1/2007 | Michaels et al. |
| D535,379 | S | 1/2007 | Hundertmark |
| 7,159,792 | B2 | 1/2007 | Wheatley et al. |
| D544,080 | S | 6/2007 | Carlson |
| D544,084 | S | 6/2007 | Michaels et al. |
| D544,594 | S | 6/2007 | Zobele |

(56) References Cited

U.S. PATENT DOCUMENTS

| | | |
|---|---|---|
| D544,953 S | 6/2007 | Kee |
| D546,432 S | 7/2007 | Hundertmark |
| 7,243,859 B2 | 7/2007 | Caserta et al. |
| D548,317 S | 8/2007 | Newton et al. |
| D550,345 S | 9/2007 | Weggelaar |
| D551,333 S | 9/2007 | Wu |
| 7,285,248 B2 | 10/2007 | Yamamoto et al. |
| D554,746 S | 11/2007 | Davis et al. |
| 7,293,719 B2 | 11/2007 | Wheatley |
| D562,441 S | 2/2008 | Crumble-Avery |
| D565,162 S | 3/2008 | Carlson |
| 7,344,123 B2 | 3/2008 | Pankhurst et al. |
| D565,715 S | 4/2008 | Wu |
| D568,456 S | 5/2008 | Hollingsworth |
| 7,389,943 B2 | 6/2008 | Jaworski |
| D573,706 S | 7/2008 | Zlotnik et al. |
| D574,941 S | 8/2008 | Weggelaar |
| 7,441,360 B2 | 10/2008 | Christianson et al. |
| D580,039 S | 11/2008 | Zlotnik et al. |
| D585,129 S | 1/2009 | Huang |
| D585,971 S | 2/2009 | Carrizales |
| D591,415 S | 4/2009 | Wu |
| D593,670 S | 6/2009 | Valentiono et al. |
| D594,953 S | 6/2009 | King et al. |
| D594,954 S | 6/2009 | Wheatley |
| 7,544,332 B2 | 6/2009 | De Silva et al. |
| D597,645 S | 8/2009 | Thompson |
| D598,531 S | 8/2009 | Irvin |
| D604,825 S | 11/2009 | Brandenburg |
| D607,983 S | 1/2010 | Irvin |
| 7,651,666 B2 | 1/2010 | Adair et al. |
| 7,670,566 B2 | 3/2010 | Adair et al. |
| 7,687,037 B2 | 3/2010 | Wheatley |
| 7,687,038 B2 | 3/2010 | Wheatley |
| D614,277 S | 4/2010 | Hsiao |
| D619,692 S | 7/2010 | Hami et al. |
| D619,693 S | 7/2010 | Hami et al. |
| D619,694 S | 7/2010 | Hami et al. |
| D620,573 S | 7/2010 | Hami et al. |
| D622,835 S | 8/2010 | Mendheim |
| 7,780,094 B2 | 8/2010 | Caserta et al. |
| D625,798 S | 10/2010 | Hami et al. |
| D629,881 S | 12/2010 | Valentino et al. |
| D631,534 S | 1/2011 | Kajizuka |
| D631,954 S | 2/2011 | Bertassi et al. |
| D633,610 S | 3/2011 | Wu |
| D637,275 S | 5/2011 | Baraky |
| D640,358 S | 6/2011 | Irvin |
| D640,781 S | 6/2011 | Brandenburg |
| D642,668 S | 8/2011 | Lablaine |
| D645,949 S | 9/2011 | Brandenburg et al. |
| D647,186 S | 10/2011 | Chan et al. |
| D649,237 S | 11/2011 | Bilko et al. |
| D650,057 S | 12/2011 | Riley |
| D650,058 S | 12/2011 | Riley |
| D650,892 S | 12/2011 | Wheatley |
| 8,147,761 B2 | 4/2012 | Wheatley et al. |
| D660,950 S | 5/2012 | Finlay |
| D662,581 S | 6/2012 | Savengnago |
| 8,197,761 B1 | 6/2012 | Miller-Larry |
| 8,251,299 B1 | 8/2012 | Wheatley |
| D667,100 S | 9/2012 | Hakim |
| D684,675 S | 6/2013 | Irvin |
| 8,485,454 B1 | 7/2013 | Irvin |
| 8,490,846 B1 | 7/2013 | Wheatley |
| 2001/0051234 A1 | 12/2001 | Ryan et al. |
| 2003/0097936 A1 | 5/2003 | Maleeny et al. |
| 2003/0199421 A1 | 10/2003 | Copfer |
| 2004/0197221 A1 | 10/2004 | Stanley, III |
| 2004/0265164 A1 | 12/2004 | Woo et al. |
| 2005/0084413 A1 | 4/2005 | Stanley, III |
| 2005/0127538 A1 | 6/2005 | Fabrega et al. |
| 2005/0169793 A1 | 8/2005 | Wheatley et al. |
| 2006/0043216 A1 | 3/2006 | Robinson |
| 2006/0078477 A1 | 4/2006 | Althoe et al. |
| 2006/0196964 A1 | 9/2006 | Wheatley et al. |
| 2006/0279008 A1 | 12/2006 | Jursich |
| 2007/0051826 A1* | 3/2007 | Schofield ........................ 239/60 |
| 2007/0057084 A1 | 3/2007 | Vieira |
| 2007/0160492 A1 | 7/2007 | Spector |
| 2007/0231508 A1 | 10/2007 | Fand et al. |
| 2007/0290064 A1 | 12/2007 | Majerowski et al. |
| 2008/0099576 A1 | 5/2008 | Hart |
| 2008/0128925 A1 | 6/2008 | Pankhurst et al. |
| 2008/0311315 A1 | 12/2008 | Marlow |
| 2008/0311316 A1 | 12/2008 | Marlow |
| 2009/0008411 A1 | 1/2009 | Schumacher et al. |
| 2009/0010813 A1 | 1/2009 | Wang et al. |
| 2009/0072045 A1 | 3/2009 | Wheatley et al. |
| 2009/0173799 A1 | 7/2009 | Litten-Brown et al. |
| 2010/0010409 A1 | 1/2010 | Irvin |
| 2010/0019059 A1 | 1/2010 | Bulsink et al. |
| 2010/0065654 A1 | 3/2010 | Wheatley |
| 2010/0187327 A1 | 7/2010 | Irvin |
| 2010/0288847 A1 | 11/2010 | Gruenbacher et al. |
| 2011/0108632 A1 | 5/2011 | Brandenburg et al. |
| 2011/0110823 A1 | 5/2011 | Wheatley et al. |
| 2012/0076276 A1 | 3/2012 | Wang et al. |
| 2013/0028798 A1 | 1/2013 | Irvin |

FOREIGN PATENT DOCUMENTS

| | | |
|---|---|---|
| EP | 1 346 734 | 9/2003 |
| WO | WO 00/24434 | 5/2000 |
| WO | WO 00/64498 | 11/2000 |
| WO | WO 02/35975 | 5/2002 |
| WO | WO 02/38029 | 5/2002 |
| WO | WO 2004/078219 | 9/2004 |
| WO | WO 2006/010282 | 2/2006 |
| WO | WO 2006/084160 | 8/2006 |
| ZA | 20004637 | 9/2000 |

OTHER PUBLICATIONS about.com Housekeeping, http://housekeeping.about.com/od/pr...affresh, Febrezee Noticeables, accessed Oct. 2, 2008, 2 pages.
Aromate E-News, Innovation in Novelty Fragrance, Http://209.85.173.104/seasrch?qcach . . . , accessed Oct. 8, 2008, 2 pages.
Ecrater, www.ecrater.com/product.hp? . . . , Yankee Candle Selects Two Scents Electric Fragrance Unit Macintosh/Home Sweet Home, accessed Oct. 2, 2008, 1 page.
http://decomodo.com/articles/categor/lighting/, Bamboo Pillar Candle, Jan. 8, 2008, 1 page.
http://shop.advanceautoparts.com/webapp/wcs/stores/servlet/product_6170795-P_N3004...Advance Auto Part; Arometrics Dual-Scent Vent—Juicy Strawberry and Vanilla; 1 Page ; accessed Dec. 10, 2010.
http://www.bestliquidations.com/Medo_Vent Frehser.htm; BestLiquidations.com; Medo Vent Fresh Air Fresheners; 2 pages; accessed Dec. 10, 2010.
Medo® Air Fresheners; Auto Expressions™ 2005 Product Catalog; 25 pages.
Pictures (3) of Medo® auto Expressions Vent™ Air Freshener distributed by SOPUS Products of Moorpark , CA 2003 copyright date on package.
Scents & Sprays, www.scentsandsprays.com/ya . . . , Yankee Autumn Bounty Electric 2 Home Air Fresheners, copyright 2001-2008 scentsandsprays.com, accessed Oct. 2, 2008, 1 page.
www.4imprint.com/EXEC/DETAIL/FROMPRODUCTGROUP/~SKU100300/~CA100300.htm, Hot Rod Vent Stick Air Freshener (it . . . , accessed Aug. 12, 2008, 2 pages.
www.autothing.com/Products/Air%20Fresheners/air%20freshenerclip.htm, Air Fresheners, Fresh Scents for you mobile Life, Clip-on Air Vent Clips rom Eagle o., Accessed Aug. 12, 2008, 1 Page.
www.chicscents.com/Products.aspx Island Adventure Sandals; 2 pages; accessed Feb. 1, 2011.
www.chicscents.com/Products.aspx; Inspiration 3-D by Chic; 2 pages; accessed Feb. 1, 2011.
U.S. Appl. No. 12/979,795, filed Dec. 28, 2010; Aaron Irvin.
U.S. Appl. No. 12/979,813, filed Dec. 28, 2010; Aaron Irvin.

(56) References Cited

OTHER PUBLICATIONS

U.S. Appl. No. 13/191,966, filed Jul. 27, 2011; Aaron Irvin.
U.S. Appl. No. 13/958,767, filed Aug. 5, 2013; Alan J. Wheatley.
U.S. Appl. No. 13/281,890, filed Oct. 26, 2011; Aaron Irvin.
U.S. Appl. No. 13/282,035, filed Oct. 26, 2011; Nathaniel Finlay.
U.S. Appl. No. 13/688,970, filed Nov. 29, 2012; Bryce Haymond.
U.S. Appl. No. 13/722,782, filed Dec. 20, 2012; Nathaniel Finlay.
U.S. Appl. No. 13/732,602, filed Jan. 2, 2013; Nathaniel Finlay.
U.S. Appl. No. 14/039,595, filed Sep. 27, 2013; Nathaniel Finlay.
U.S. Appl. No. 13/732,584, filed Jan. 2, 2013; Aaron Irvin.
U.S. Appl. No. 13/744,253, filed Jan. 17, 2013; Nathaniel Finlay.
U.S. Appl. No. 13/798,912, filed Mar. 13, 2013; Aaron Irvin.
U.S. Appl. No. 13/798,793, filed Mar. 13, 2013; Aaron Irvin.
U.S. Appl. No. 29/452,344, filed Apr. 15, 2013; Aaron Irvin.
U.S. Appl. No. 13/940,074, filed Jul. 11, 2013; Alan J. Wheatley.

\* cited by examiner

AIR FRESHENER WITH DECORATIVE INSERT

PRIORITY CLAIM(S)

Priority is claimed to U.S. Provisional Patent Application Ser. No. 61/717,527, filed Oct. 23, 2012, which is hereby incorporated herein by reference.

Priority is claimed to U.S. Provisional Patent Application Ser. No. 61/717,520, filed Oct. 23, 2012, which is hereby incorporated herein by reference.

RELATED APPLICATION(S)

This is related to U.S. Design patent application Ser. Nos. 29/452,344 and 29/452,343, both filed Apr. 15, 2013; which are hereby incorporated herein by reference.

BACKGROUND

1. Field of the Invention

The present invention relates generally to air fresheners.

2. Related Art

Air fresheners are common devices used to improve and/or change the olfactory characteristics of an environment. Such environments can include bathrooms or wash closets, vehicles, lockers, drawers, etc. Such air fresheners typically include a scent that is aesthetically pleasing, such as flowers, fruits, etc.

One common type of air freshener is a two-dimensional, paper-fiber card with a fragrance surrounded in a clear plastic envelope. The envelope is pierced to form an opening, and a portion of the freshener protrudes through the opening to release a scent. The air freshener includes a string or elastic forming a loop to suspend the air freshener. Such air fresheners are commonly utilized in vehicles. One disadvantage with such air fresheners is that the card is moist, and can leak or leach, leaving a stain on other surfaces, such as dashboards. The plastic envelope and the suspending loop act to resist contact between the card, and other surfaces. Another disadvantage with such air fresheners is that they are aesthetically displeasing. Another disadvantage with such air fresheners is that they have a more pronounced and immediate scent release, releasing a majority of the scent in the first few days of use.

Another common type of air freshener has a disc-shaped shell or canister with a scented disc or gel inside. The shell can include an adhesive strip to stick or adhere the shell to a surface. One disadvantage with such air fresheners is that removal of the shell often leaves a residue of the adhesive on the surface, which is aesthetically displeasing. In addition, the scented material can leak and harm the surface.

Some disadvantages of common air fresheners include 1) rapid scent loss or lack of longevity; 2) non-linear or inconsistent scent release over time; and 3) risk of staining. Some air fresheners disperse their scent too rapidly, thus losing effectiveness over time, and not lasting as long as desired. Some air fresheners quickly or rapidly disperse their scent after activation, and then slowly release scent, or release little scent, thereafter. Some air fresheners include materials that can leak and stain.

Another disadvantage with some air fresheners is that they include a non-solid and non-liquid material, or a jelly-like material, that must be contained in some type of container because the jelly is flowable. The material can become dried and cracked over time, presenting an aesthetically displeasing appearance. Again, the scented material can leak and damage surfaces.

SUMMARY OF THE INVENTION

It has been recognized that it would be advantageous to develop an air freshener.

The invention provides an air freshener comprising a rigid body having a front face with a protrusion, a rear opposite the front face with a cavity corresponding to the protrusion, and an annular perimeter lip circumscribing the front face. A scent material is interspersed within the body. A flexible cover extends across the rear of the body and covers the cavity and has an inward facing annular groove surrounding and receiving the annular perimeter lip.

In addition, the invention provides an air freshener comprising a pair of shells with a pair of cavities facing one another, including a larger shell with a larger perimeter, and a smaller shell with a smaller perimeter disposed in the cavity of the larger shell. An outward projecting perimeter lip circumscribes the smaller shell. An inward projecting perimeter flange circumscribes the cavity of the larger shell and forms an inwardly facing annular groove receiving the perimeter lip of the smaller shell. The smaller shell is relatively rigid with respect to the larger shell, and the larger shell is relatively flexible with respect to the smaller shell. The larger shell is flexible to expand over the perimeter lip of the smaller shell. A scent material is interspersed within the smaller shell.

Furthermore, the invention provides an air freshener comprising a shell with cavity formed in the shell. The shell with the cavity therein have matching perimeter shapes. An insert is disposed in the cavity and has a perimeter shape matching the perimeter shapes of the shell and the cavity. The insert and the shell are formed of different materials. The shell is larger than the insert and circumscribes the insert. A scent material is interspersed within the insert. An aperture extends through the shell and the insert. A hanger extends through the aperture with the shell and the insert suspended therefrom. A protrusion extends from the insert.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The term "scent material" and "fragrant material" are used interchangeably herein to refer broadly to a material that carries a desired fragrance or scent that can be discernable or smelled, or even a neutralizing agent. Thus, the scent or fragrance can be an ascertainable smell used to cover other scents, or a neutral agent that eliminates odors or provides a fresher atmosphere.

DESCRIPTION

Figure 1:
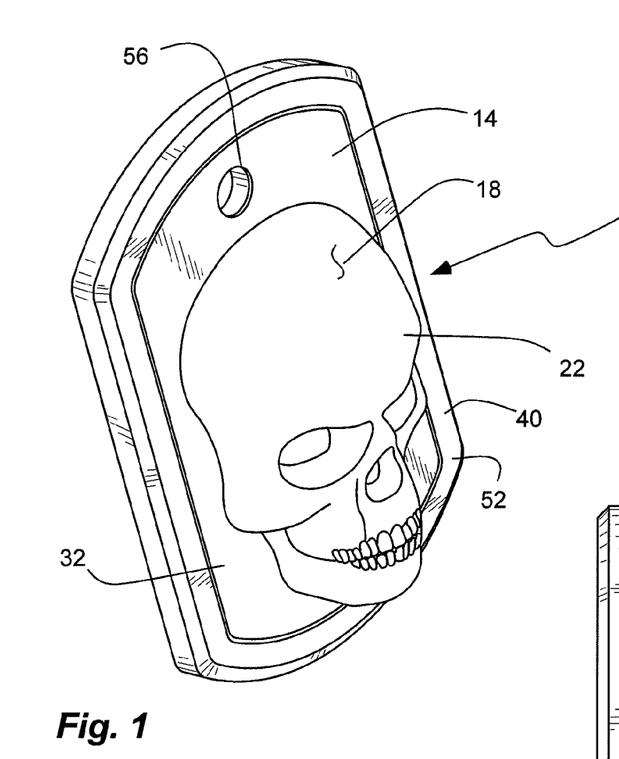
FIG. 1 is a perspective view of an air freshener in accordance with an embodiment the present invention.
Figure 2:
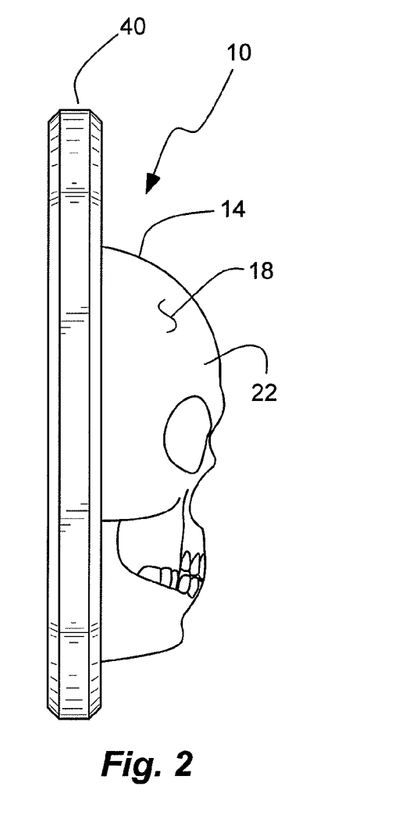
FIG. 2 is a side view of the air freshener of FIG. 1.
Figures 3, 4:
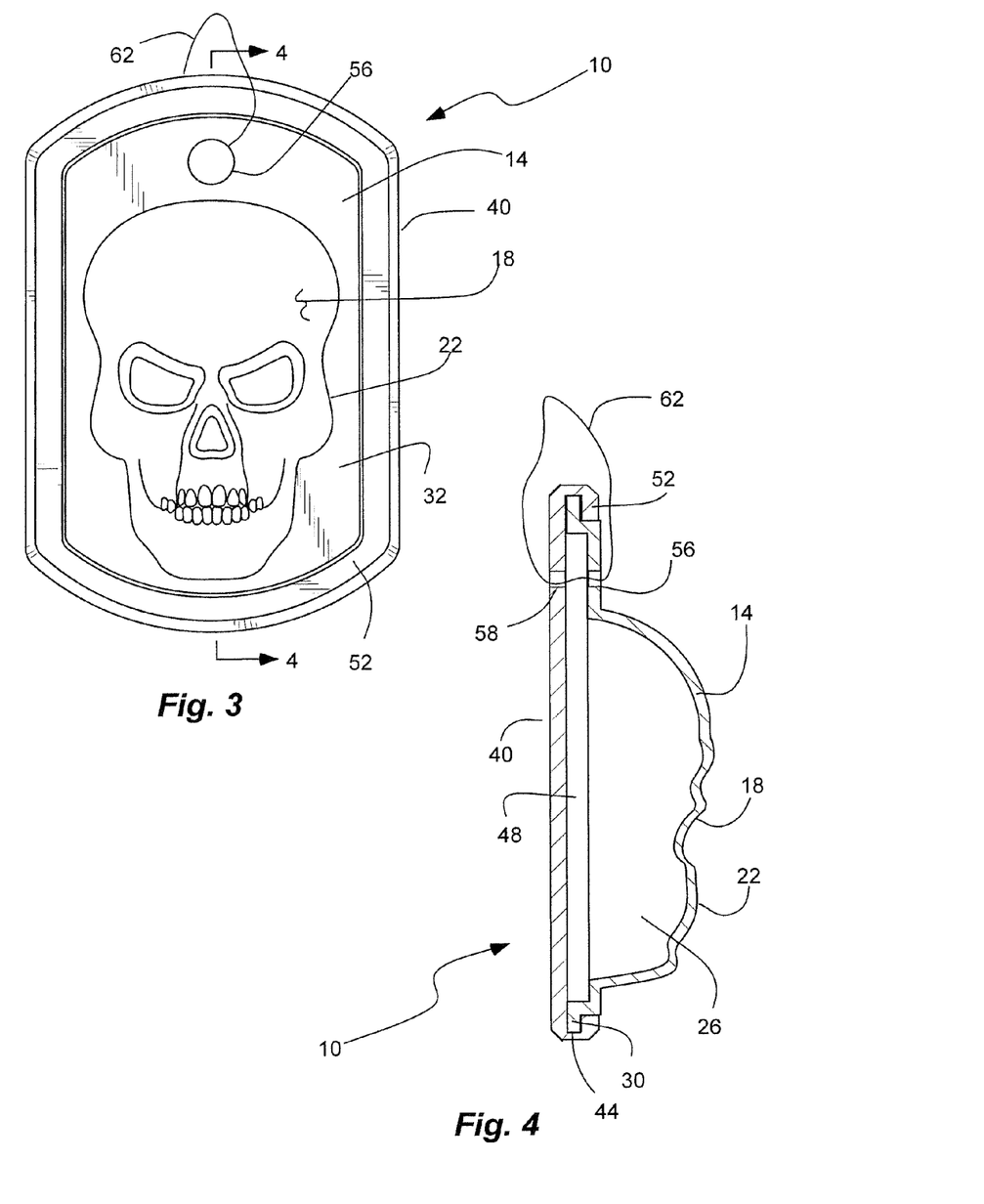
FIG. 3 is a front view of the air freshener of FIG. 1.
FIG. 4 is a cross-sectional side view of the air freshener of FIG. 1 taken along line 4 of FIG. 3.
Figure 5:
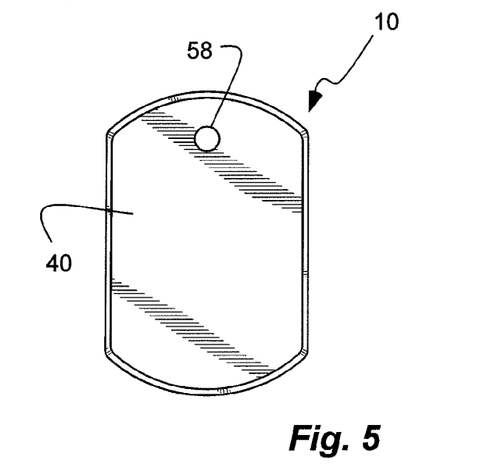
FIG. 5 is a rear view of the air freshener of FIG. 1.
Figure 6:
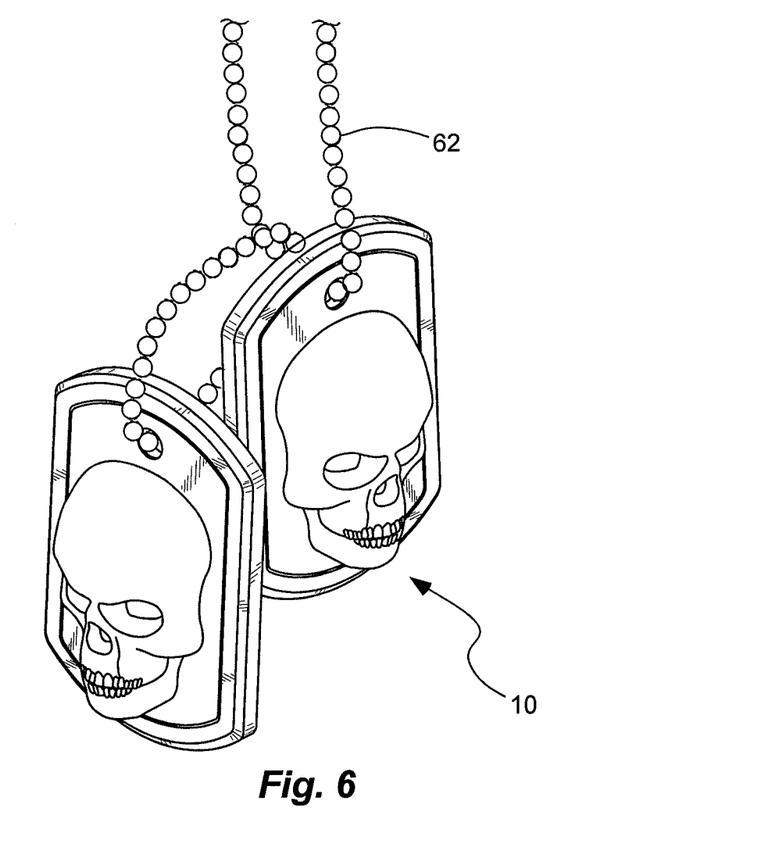
FIG. 6 is a perspective view of the air freshener of FIG. 1 shown in use with a pair of air fresheners.

As illustrated in FIGS. 1-6, an air freshener or scent device, indicated generally at 10, in accordance with the present invention is shown for providing a desired and/or aesthetically pleasing scent, fragrance, aroma or neutralizing agent, as well as an aesthetically pleasing visual air freshener. Air fresheners are one example of a field that can benefit from the present invention. The air freshener 10 can be configured for use in vehicles, and can also be used in bathrooms, wash closets, offices, bedrooms, etc. The desired scent can include, for example, floral, fruit, vanilla, berry, pine, etc. The air freshener can have a body and a cover, or a pair of shells, with complimentary shapes that together form a unified shape. The unified shape of the body can form a novelty item. A scent material is interspersed within one or both of the body, cover and/or shells.

The air freshener 10 can have a rigid body 14 that defines a smaller shell. The body 14 or smaller shell can have a front face 18 with a protrusion 22. In addition, the body 14 or shell can have a rear that is opposite the front face, and which has a cavity 26 (FIG. 4) corresponding to the protrusion 22. Furthermore, the body 14 or smaller shell can have an annular perimeter lip 30 (FIG. 4) circumscribing the front face 18, the protrusion 22 and/or the cavity 26. The annular perimeter lip 30 can be a radially outward projecting perimeter lip. The annular perimeter lip 30 and/or the body 14 can have a shape that forms a novelty item, such as dog tags, as shown. Thus, the body 14 and/or annular perimeter lip 30 or the shape thereof can include parallel straight sides and convex arcuate ends. In addition, the protrusion 22 can have a shape that corresponds to the novelty item, including a skull, as shown. The body 14 and/or the front face 18 can have a perimeter portion 32 that is flat and circumscribes the protrusion 22. The body 14 or smaller shell can be a smaller shell with a smaller diameter, as discussed in greater detail below. The body 14 or smaller shell can be formed of a metal or metallic material. A scent material can be interspersed within the body, the smaller shell, and/or the metal material thereof. The scent or fragrance of the scent material can escape from the body 14 or shell over time to provide an aesthetically pleasing smell. The protrusion 22 in the front face 18 of the body 14 can provide increased surface area for scent release, while the cavity 26 can reduce the weight and material costs of the air freshener.

The air freshener 10 can also have a flexible cover 40 that defines a larger shell. The flexible cover 40 or larger shell extends across the rear of the body 14, and covers the cavity 26 of the body or smaller shell. The front face of the body can be or remain exposed by the cover. The cover 40 can have a radially inward facing annular groove 44 (FIG. 4) surrounding and receiving the annular perimeter lip 30 of the body 14. In addition, the cover can have a cavity 48 (FIG. 4) facing the cavity 26 of the body. The groove 44 of the cover 40 can include a radially inward projecting perimeter flange 52 that circumscribes the cavity 48 of the cover 40 or larger shell, and forms the groove 44. The flange 52 of the cover 40 can be flat and flush with the front face 18 of the body 14 or a perimeter portion 32 thereof that is flat. The flush surfaces can resist tampering and removal of the cover. Thus, the perimeter of the body 14 can be stepped to be flush with the cover, or the annular perimeter lip 30 of the body can be stepped with respect to the perimeter portion 32 of the front face 18 of the body. The perimeter of the cover 40 can have a shape that corresponds to a shape of the body 14, and together they can form the novelty item, such as dog tags, as shown. The perimeter of the cover 40 or the shape thereof can include parallel straight sides and convex arcuate ends. The cover 40 and cavity 48 thereof can be flat and shallow. The cover 40 can be a larger shell with a larger perimeter. Thus, the body 14 and cover 40 can form a pair of shells with a pair of cavities facing one another including a larger shell with a larger perimeter and a smaller shell with a smaller perimeter disposed in the cavity of the larger shell. The cover 40 can be flexible and elastic, and can be formed of or can include plastic. Thus, the flange 52 and/or or groove 44 of the cover can be flexible to stretched over the lip 30 of the body 14 and resilient or elastic to maintain the cover on the body. The two cavities 26 and 48 can form a cavity of the air freshener 10. The cover 40 can resist the body 14 from contacting other surfaces to resist leaching or wicking of the scent material from the body. In addition, the cover can be softer than the body and can resist the body from impacting other surface, such as when hung from a rear view mirror (see FIG. 6).

An aperture 56 and 58 can extending through the body 14 and the cover 40 to receive a hanger 62 to suspend the body and the cover therefrom.

Although the scent material has been described as being in the body or smaller shell, the scent material can also be in the cover or larger shell, or both the body and the shell.

The flexible cover 40 can form a shell with a cavity therein having matching perimeter shapes, and the rigid body 14 can form an insert disposed in the cavity and having a perimeter shape matching the perimeter shapes of the shell and the cavity.

Figure 7:
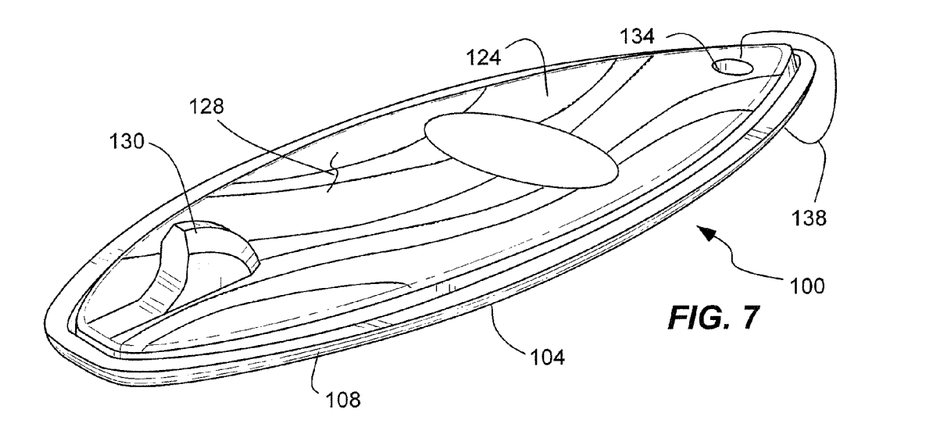
FIG. 7 is a perspective view of another air freshener in accordance with another embodiment of the present invention.
Figure 8:
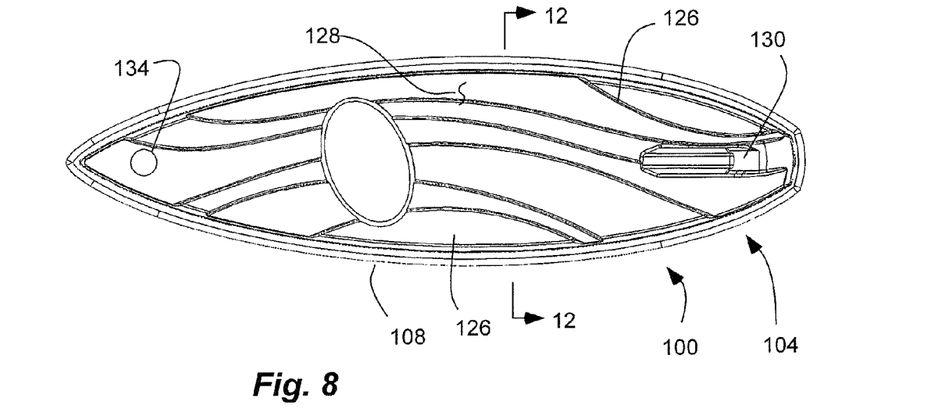
FIG. 8 is a bottom view of the air freshener of FIG. 7.
Figure 9:
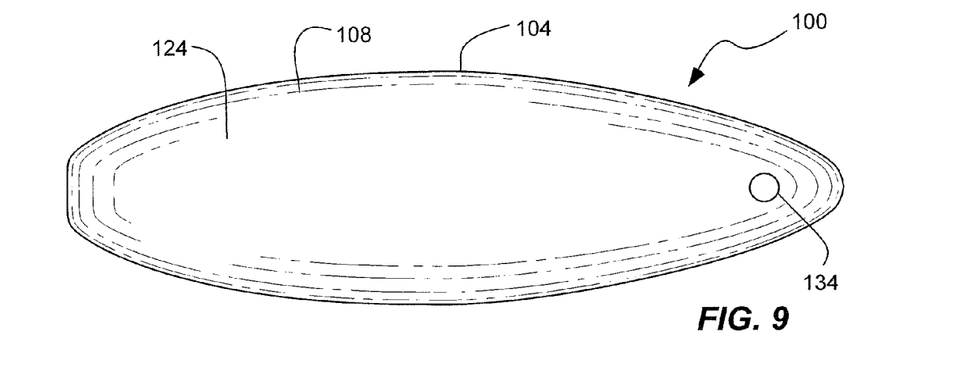
FIG. 9 is a top view of the air freshener of FIG. 7.
Figures 10, 11, 12, 13:
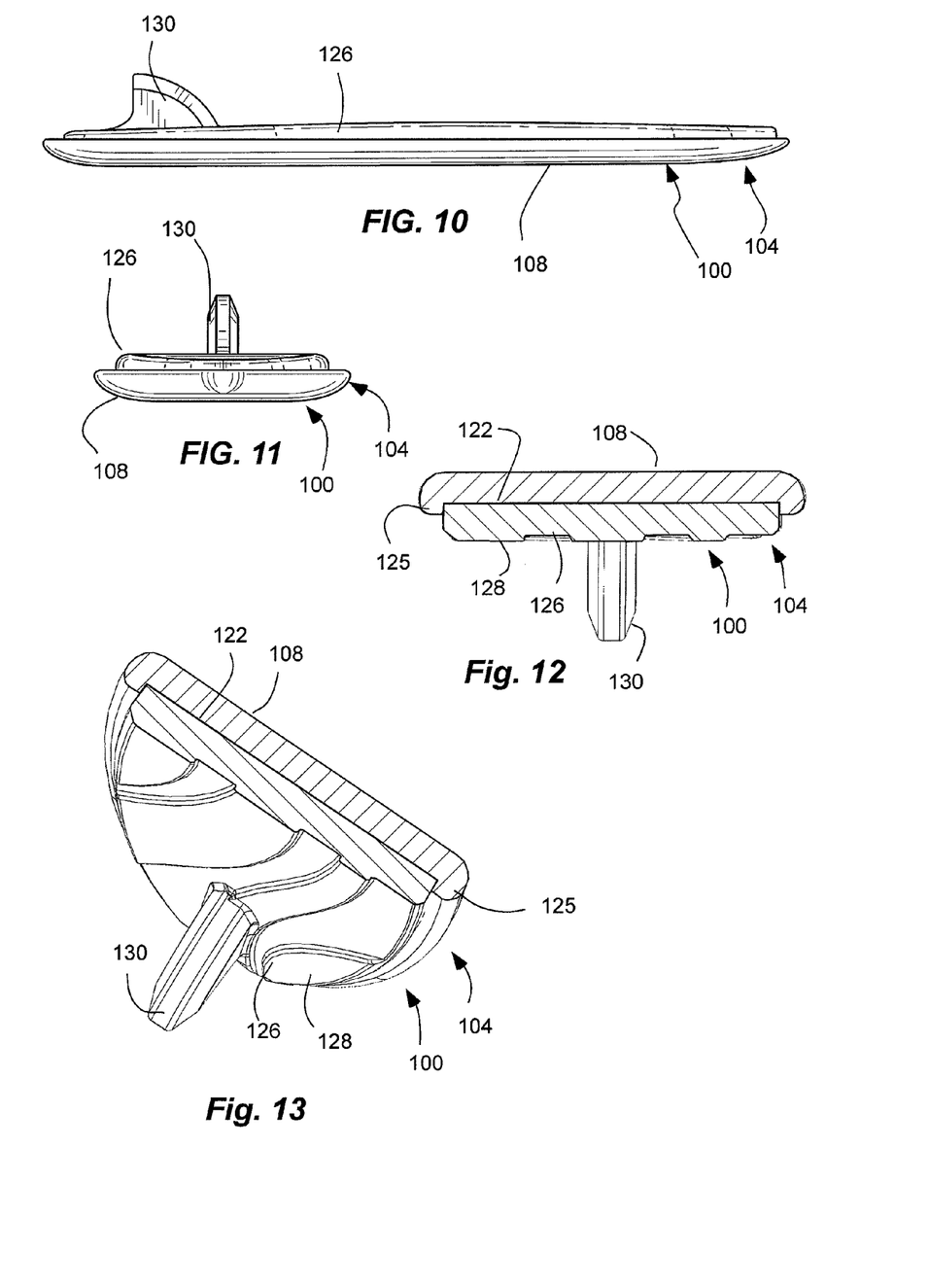
FIG. 10 is a side view of the air freshener of FIG. 7.
FIG. 11 is an end view of the air freshener of FIG. 7.
FIG. 12 is a cross-sectional end view of the air freshener of FIG. 7 taken along line 12 of FIG. 8.
FIG. 13 is a cross-sectional perspective view of the air freshener of FIG. 7 taken along line 12 of FIG. 8

As illustrated in FIGS. 7-13, another air freshener or scent device, indicated generally at 100, in accordance with the present invention is shown for providing a desired and/or aesthetically pleasing scent, fragrance, aroma or neutralizing agent, as well as an aesthetically pleasing visual air freshener. As described above, the air freshener can be configured for use in vehicles, and can also be used in bathrooms, wash closets, offices, bedrooms, etc. The air freshener can have a body including a shell with a cavity and an insert disposed in the cavity with the insert and the shell having complimentary shapes that together form a body with a unified shape. A scent material is interspersed within the insert. The unified shape of the body forms a novelty item.

The air freshener 100 can have a body 104 including a shell 108 with a cavity 122 (FIGS. 12 and 13) formed in the shell. The cavity 122 can be formed in the body 104 to form the shell 108. Thus, the shell 108 can have a shell wall with a substantially constant wall thickness. The shell 108 can have an exterior surface 124 that can be flat and/or smooth. Alternatively, the exterior surface of the shell can be contoured, such as with protrusions and/or indentations. The shell 108 and the cavity 122 can have matching perimeter shapes. The shell 108 can have an opening into the cavity with the opening substantially matching the shape of the shell. Thus, the shell 108 and the cavity 122 and/or opening can have substantially the same shape. A perimeter flange 125 (FIGS. 12 and 13) can be formed in the shell that extends around the cavity 122 so that the cavity is bordered or circumscribed by the flange or portion of the shell. The flange 125 can have a perimeter shape that matches the shell and the cavity. The cavity 122 can be shallow and/or flat, with a height and a width, or diameter or lateral size, greater than a depth.

An insert 126 is disposed in and fills the cavity 122. The insert 126 can have a perimeter shape that matches the perimeter shapes of the shell 108 and the cavity 122. Thus, the insert 126 can substantially fill the cavity 122. In addition, the insert 126 can be broad and flat, with a height and a width, or diameter or lateral size, equal to or greater than the depth of the cavity. Thus, the insert 126 can extend out of and/or protrude from the cavity 122 and opening thereof. The insert extending out of the cavity can increase the exposed surface area to increase scent release. The shell 108 can be larger, or have a lateral size, greater than the lateral size of the insert 126 so that shell circumscribes the insert. The insert can be or can remain exposed by the shell. A scent material can be interspersed within the insert 126. The scent or fragrance of the scent material can escape from the body 104 or shell over time to provide an aesthetically pleasing smell. The insert 126 can have an exterior surface 128 that can be contoured, such as with protrusions and/or indentations. The contoured shape of the exterior surface can create a greater surface area to increase scent release. Alternatively, the exterior surface of the shell can be flat and/or smooth.

The shell 108 and the insert 126 can have complimentary shapes that together form the body 104 with a unified shape. Thus, together, the shell and the insert can form the body and/or a unified shape. Thus, the shell and the insert together can form a shape together that neither could form alone. In one aspect, the unified shape of the body 104 formed by the shell 108 and the insert 126 can be a scaled down surfboard with the shell forming a top of the surfboard, and the insert forming a bottom of the surfboard. The insert can also include a protrusion 130 extending from the insert. The protrusion can form a fin of the surfboard. The protrusion 130 can increase the surface area of the insert, and thus increase scent release. The surfboard or shell can have a long dimension less than 5 inches. The shell and the insert can be substantially flat. A decal can be disposed on the shell, or exterior surface thereof, opposite the cavity. In another aspect, the unified shape of the body can form another novelty item.

The insert 126 and the shell 108 can be formed of different materials. For example, the shell 108 can be made of or can include wood, while the insert 126 can be formed of or can include plastic.

The shell 108 can circumscribe the insert 126. The shell 108 can resist the insert 126 from contacting other surfaces to resist leaching or wicking of the scent material from the insert. In addition, the shell can resist the insert from impacting other surface, such as when hung from a rear view mirror.

An aperture 134 can extend through the shell 108 and the insert 126. A hanger 138 can extend through the aperture with the shell and the insert suspended therefrom. A method for refreshing a space in a vehicle or otherwise using an air freshener device described above includes hanging the hanger of the air freshener device from a rear view mirror of the vehicle.

As described above, the air freshener 10 or 100 in FIGS. 1-6 and FIGS. 7-13, respectively, can have a shell with an insert. The flexible cover 40 of the air freshener 10 of FIGS. 1-6 can be the shell and the rigid body 14 can be the insert.

As described above, a scent material with a desired scent or fragrance can be associated with and carried by the body or insert. The scent material can be in a polymer body or carrier material carried by the body or insert. The insert can be the carrier material or polymer body. In one aspect, the insert or carrier material can be a single insert. In another aspect, the insert or carrier material can include multiple inserts. The insert can have an exposed side or surface with indicia thereon. The insert can be adhered to the shell in the cavity. In another aspect, the shell can have a plurality of protrusions, and the insert can have a plurality of apertures corresponding to the protrusions. In another aspect, the protrusions can be formed on the insert, and the apertures can be formed in the shell. The insert can be coupled to the shell by snapping the apertures onto the protrusions.

The insert or polymer body can be flexible and resilient, such as a polymer gel. The polymer body can be elastic and coherent. Thus, the polymer body can be compressible under an applied force, and substantially returnable to an original configuration upon removal of the applied force. It has been found that the polymer gel provides desired characteristics of aesthetics, flexibility, longevity, substantially constant scent release, and containment. In accordance with another aspect of the present invention, the polymer gel can have a freestanding, self-supported, three-dimensional shape that does not significantly change as the scent is released. The carrier material or polymer body can have a scent material of the desired scent interspersed therein. The scent material disperses or diffuses out of the carrier material or polymer body into the air or atmosphere where it can be detected, or where it can provide a discernable scent. It is believed that the scent material migrates or diffuses through and out of the carrier material or polymer body. The scent material can be high in volatile notes, or has high volatility and can vaporize or evaporate at low temperatures. The scent material can include a scented oil. For example, suitable scent material can include pine, berry, vanilla, apple, coconut, cherry, pina colada, etc.

The carrier material or polymer body can include a polymer material, such as a polymer gel. The polymer body and/or polymer gel can be elastic and coherent. Thus, the polymer body can elastically deform under normal conditions. The polymer body can be flexible and resilient, such that the body or gel can compress under an applied force, but can substantially return to its original configuration upon removal of the applied force. The polymer gel, or the polymer body, can have a freestanding, self-supported, three-dimensional shape. Thus, the polymer gel or polymer body can be consistent or solid enough to support or maintain its shape in a freestanding manner without a container. The three-dimensional shape can be any desired shape. The polymer gel can be considered a solid material that is elastic and coherent, and thus flexible and capable of being deformed, but without being flowable. Thus, the polymer gel may have a sufficiently high molecular weight, and/or a sufficiently high viscosity, so that it is a non-flowable gel. In addition, the polymer gel can be considered as stable. Thus, the polymer gel can be bendable, but otherwise substantially maintains its form. The polymer body or polymer gel can be characterized as a polymeric material in the glass state with substantially no macroscopic flow. The polymeric material can have a glass transition temperature greater than approximately 110° F. The polymer gel can retain its gel-like characteristic over time, without drying or cracking, and without becoming hard or brittle.

In one embodiment, the polymer gel or polymer body can include a polyurethane material or can be a polyurethane gel. The gel can be formed by combining a polyurethane material with a scented oil. Surprisingly, it has been found that such a combination provides a desired scent, but without staining or substantially leaking onto a surface. In addition, the polymer body does not undergo a visually ascertainable physical change, such as drying out or cracking. Thus, the polymer body remains aesthetically pleasing.

In some embodiments, a scented oil and a polymerizable monomer can be combined, along with optional initiators or other reactants. Isocyanate reaction polymers have shown good results in connection with the present invention. For example, the polymer gel and scent material can be a urethane polymerization product of combining a scented oil with a polyether polyol, and then with a diphenylmethane diisocyanate (MDI) prepolymer. Therefore, in some embodiments, the scent material can be a scented oil which participates in the polymerization reaction between polymerization reactants. For example, essential oils such as terpenes and the like can be mixed with polymerization reactants, or even in place of some reactants. Without being bound by any particular theory, it is thought that at least some of the reduction or elimination in residue in the devices of the present invention result from at least partial replacement of mineral oils and/or polyols with scented oils such as those listed herein. Other suitable isocyanates can include, but are not limited to, tolylene diisocyanates, methylene diphenyl isocyanates, hexamethylene diisocyanates, prepolymers thereof, and the like. Those skilled in the art will recognize various other isocyanate reaction polymers, i.e. polyurethanes, which can be suitable for use in connection with the present invention.

Alternatively, the polymer gel or polymer body can include silicone, diffused polyurethane, polyvinylchloride (PVC), ethylene vinyl acetate (EVA), thermoplastic polyurethane (TPU), a polymer encapsulation fragrance delivery platform (PolyIFF®), thermoplastic elastomer (TPE), polypropylene, ethylene/methacrylic acid (E/MAA) copolymer, in which the MAA groups have been partially neutralized with lithium ions (Surlyn® Dupont), etc.

As a general guideline, the polymer gel or polymer body can be formed of an elastomer such as, but not limited to, urethanes (including polyester and polyether polyol/isocyanate polymerization products), polyacrylates, polybutadienes, ethylene propylene elastomers, silicones, natural and synthetic rubbers, styrene/butadiene block copolymers, and the like. In some embodiments, the polymer gel can be formed of a thermoplastic elastomer. Thermoplastic elastomers can be block copolymers such as polyurethanes, polyamides, copolyesters, and styrene-butadiene-styrene polymers. Other thermoplastic elastomers can be elastomer/thermoplastic blends such as ethylene-propylene-diene monomer in an isotactic polypropylene phase or nitrile rubber dispersed in a PVC phase. As used herein, "thermoplastic elastomer" refers to an elastomer which can be heated and processed like thermoplastic materials. Specifically, a thermoplastic elastomer can be heated to a melted or flowable state and then cooled, resulting in reformation of cross-linking and subsequent coherency without a substantial change in mechanical properties such as strength, flexural modulus, elastic modulus, etc.

As used herein, "elastomeric polymer" and "elastomer" may be used interchangeably and refer to a polymeric material which can be mechanically deformed and upon release returns to an original shape. A coherent elastomer is also non-flowable at or near room temperatures.

Although the polymer gel or polymer body is freestanding and self-supporting, it is also flexible and resilient. Thus, polymer body or carrier material can form a flexible and resilient structure or body that can be selectively deformed and can return substantially to the three-dimensional shape. In addition, the carrier material or polymer body can be opaque. Alternatively, the carrier material or polymer body can be light transmissive in at least a translucent manner.

In another aspect, the shell can also include a scent material. The scent material of the shell and the scent material of the insert can be different but complimentary.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An air freshener device, comprising:
   a) a rigid body having a front face with a protrusion, a rear opposite the front face with a cavity corresponding to the protrusion, and an annular perimeter lip circumscribing the front face;
   b) a scent material interspersed within the body;
   c) a flexible cover extending across the rear of the body and covering the cavity and having an inward facing annular groove surrounding and receiving the annular perimeter lip;
   d) an aperture extending through the body and the cover; and
   e) a hanger extending through the aperture with the body and the cover suspended therefrom.

2. The air freshener device in accordance with claim 1, wherein the annular perimeter lip has parallel straight sides and convex arcuate ends.

3. The air freshener device in accordance with claim 1, wherein the body includes a metal material and the cover includes plastic.

4. The air freshener device in accordance with claim 1, wherein the cover is substantially flat.

5. The air freshener device in accordance with claim 1, wherein the front face of the body has a perimeter portion that is flat and flush with a flat perimeter portion of the cover.

6. An air freshener device, comprising:
   a) a pair of shells with a pair of cavities facing one another including a larger shell with a larger perimeter and a smaller shell with a smaller perimeter disposed in the cavity of the larger shell;
   b) an outward projecting perimeter lip circumscribing the smaller shell;
   c) an inward projecting perimeter flange circumscribing the cavity of the larger shell and forming an inwardly facing annular groove receiving the perimeter lip of the smaller shell;
   d) the smaller shell being relatively rigid with respect to the larger shell and the larger shell being relatively flexible with respect to the smaller shell, the larger shell being flexible to expand over the perimeter lip of the smaller shell;
   e) a scent material interspersed within the smaller shell;
   f) a front face of the smaller shell having a perimeter portion that is flat and flush with a flat perimeter portion of the larger shell.

7. The air freshener device in accordance with claim 6, wherein the perimeter lip has parallel straight sides and convex arcuate ends.

8. The air freshener device in accordance with claim 6, wherein the smaller shell includes a metal material and the larger shell includes plastic.

9. The air freshener device in accordance with claim 6, wherein the larger shell is substantially flat.

10. The air freshener device in accordance with claim 6, further comprising:
   a) an aperture extending through the smaller shell and the larger shell; and
   b) a hanger extending through the aperture with the smaller shell and the larger shell suspended therefrom.

11. An air freshener device, comprising:
   a) a shell;
   b) a cavity formed in the shell;
   c) the shell with the cavity therein having matching perimeter shapes;
   d) an insert disposed in the cavity and having a perimeter shape matching the perimeter shapes of the shell and the cavity;
   e) the insert and the shell being formed of different materials;
   f) the shell being larger than the insert and circumscribing the insert;
   g) a scent material interspersed within the insert;
   h) an aperture extending through the shell and the insert;
   i) a hanger extending through the aperture with the shell and the insert suspended therefrom; and
   j) a protrusion extending from the insert.

12. The air freshener device in accordance with claim 11, wherein
   the insert fills the cavity; and
   the shell and the insert having complimentary shapes that together form a body with a unified shape.

13. The air freshener device in accordance with claim 11, wherein the shell comprises wood and the insert comprises plastic.

14. The air freshener device in accordance with claim 11, wherein the shell and the insert are substantially flat.

15. The air freshener device in accordance with claim 11, wherein the insert protrudes from the cavity of the shell.

16. The air freshener device in accordance with claim 11, wherein:
   a) the insert has a rigid body with a front face, a rear opposite the front face with a cavity corresponding to the protrusion, and an annular perimeter lip circumscribing the front face; and
   b) the shell is a flexible cover extending across the rear of the body and covering the cavity and having an inward facing annular groove surrounding and receiving the annular perimeter lip.

17. The air freshener device in accordance with claim 11, wherein:
   a) the shell and the insert are a pair of shells with a pair of cavities facing one another including a larger shell with a larger perimeter and a smaller shell with a smaller perimeter disposed in the cavity of the larger shell;
   b) an outward projecting perimeter lip circumscribing the smaller shell;
   c) an inward projecting perimeter flange circumscribing the cavity of the larger shell and forming an inwardly facing annular groove receiving the perimeter lip of the smaller shell;
   d) the smaller shell being relatively rigid with respect to the larger shell and the larger shell being relatively flexible with respect to the smaller shell, the larger shell being flexible to expand over the perimeter lip of the smaller shell; and
   e) the scent material interspersed within the smaller shell.

* * * * *